United States Patent [19]

Zöld

[11] 4,237,416
[45] Dec. 2, 1980

[54] APPARATUS FOR COUNTING AND SIZING PARTICLES SUSPENDED IN A LIQUID ELECTROLYTE

[75] Inventor: Tibor Zöld, Munster, Fed. Rep. of Germany

[73] Assignee: Becton Dickinson and Company, Paramus, N.J.

[21] Appl. No.: 888,899

[22] Filed: Mar. 22, 1978

[30] Foreign Application Priority Data

Mar. 22, 1977 [DE] Fed. Rep. of Germany ....... 2712360
Sep. 23, 1977 [DE] Fed. Rep. of Germany ....... 2742838

[51] Int. Cl.$^2$ ........................................... G01N 27/00
[52] U.S. Cl. .............................. 324/71 CP; 73/432 PS
[58] Field of Search .............. 324/71 CP; 235/92 PC; 364/555; 73/432 PS

[56] References Cited

U.S. PATENT DOCUMENTS

| | | | |
|---|---|---|---|
| 3,361,965 | 2/1968 | Coulter et al. | 324/71 CP |
| 3,746,976 | 7/1973 | Hogg | 324/71 CP |
| 3,793,587 | 2/1974 | Thom et al. | 324/71 CP |
| 4,001,678 | 1/1977 | Berg | 324/71CP |
| 4,014,611 | 3/1977 | Simpson et al. | 324/71 CP |
| 4,070,617 | 1/1978 | Kachel et al. | 324/71 CP |

FOREIGN PATENT DOCUMENTS 1919628 4/1971 Fed. Rep. of Germany ...... 324/71 CP

Primary Examiner—Rudolph V. Rolinec
Assistant Examiner—Walter E. Snow

[57] ABSTRACT

An apparatus for counting and sizing particles suspended in a liquid electrolyte, having first and second vessels for first liquid electrolyte having particles to be counted and sized suspended therein; and for particle-free second liquid electrolyte, respectively; first and second electrodes immersed in the first and second liquid electrolytes, respectively; an orifice having upstream and downstream sides and constituting a first particle-observing location in fluid flow connection on its upstream side with the first vessel and sized to allow one particle at a time to pass therethrough; and a fluid flow passage connecting with the downstream side of the orifice for carrying liquid electrolyte and particles away from the orifice to a second particle-observing location; and sized to carry the particles in the same sequence of flow as that in which they pass through the orifice to facilitate observation in that order at the second particle-observing location.

34 Claims, 5 Drawing Figures

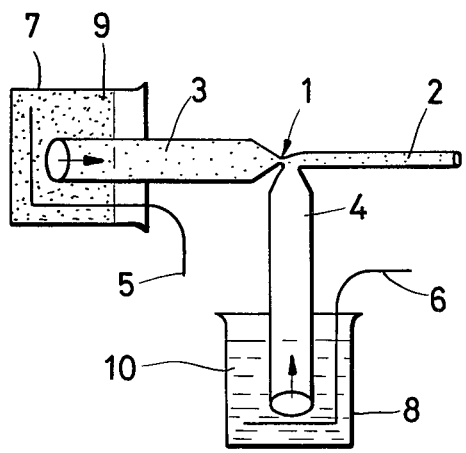
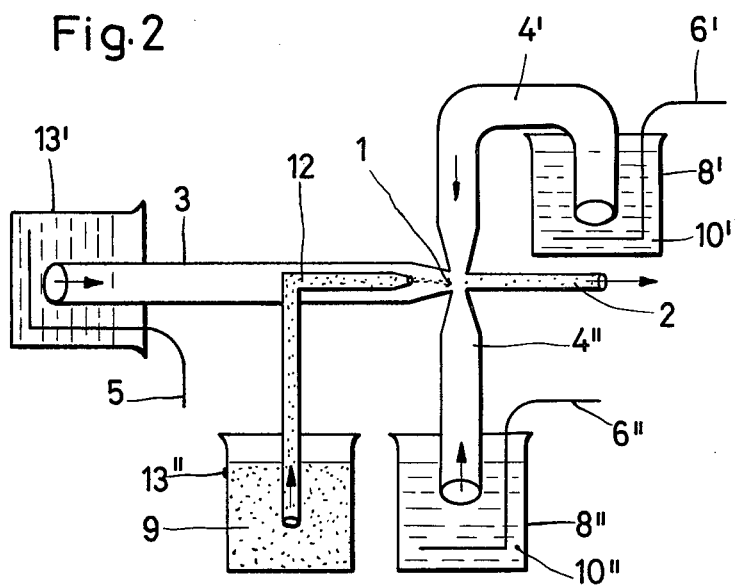

APPARATUS FOR COUNTING AND SIZING PARTICLES SUSPENDED IN A LIQUID ELECTROLYTE

This invention relates to a counter of the channel type for the counting and sizing of particles suspended in an electrolyte comprising a first electrode, an orifice, and a second electrode, the first and second electrodes, being situated in separate containers and located at the upstream and downstream sides of the orifice, respectively. Thus, the passage of a particle of different electrical conductivity than that of the electrolyte corresponds to a change in the resistance between the two electrodes mentioned above. This resistance impulse is then measured and processed further by the attached electronical equipments.

Such a device is especially very useful in cytology for the counting and sizing of cells such as tumour and blood cells, or in the study of other micro-organismae suspended in an electrolyte.

Such a counter is called "Coulter counter"; see for instance the publication "Sizing particles with a Coulter Counter" by J. Hurly in Biophys. J. vol. 10, pp. 74–79 (1970), or "Effects of External Electrical Fields on Cell Membranes" by U. Zimmermann et al., in Bioelectrochemistry and Bioenergetics, vol. 3, pp. 58–83 (1976). The principle of the above mentioned counter is as follows. If the particle of the electrolyte dispersion has a conductivity different from that of the electrolyte, then, by the passage of the particle through an orifice of very small dimensions and connecting two larger volumes where the electrodes mentioned above are located, an electric current or voltage impulse is generated in the electrical circuit connected to the electrodes situated at the upstream and downstream side of the orifice, respectively. Presently two distinctly different embodiments of the known counter are in use. In the first embodiment, the original Coulter counter, the dispersion flows from a relative large chamber through the orifice of very small dimensions relative to that of the chamber into another large second chamber and by the passage of a particle of different electrical conductivity from that of the electrolyte an electrical voltage and/or electrical current is generated in the electrical circuit connected to the electrodes located in the two large chambers. Then the impulses are amplyfied and fed to other electronical equipments, such as decade counters and/or multichannel analysing equipment.

In another embodiment of the known counter, cf. especially the work by U. Zimmermann et al. mentioned above, the dispersion flows via a capillary through the first large chamber, filled with particle free electrolyte and then through the orifice in a hydrodynamically focused form into the second large chamber as the capillary ends in a nozzle coaxially located in front of the orifice. In this manner the particles flow through a smaller, thus more homogeneous part of the electric field in the orifice, and consequently, the impulse magnitude corresponds with a greater accuracy to the particle volume than in the first embodiment where the particles can flow through any part of the orifice.

It is a disadvantage of the known counter that any particle is essentially lost in a large volume after the passage of the particle through the orifice. Therefore, further analysis of the particle in another equipment is impossible because the particle is not anymore identifiable.

Therefore, it is one object of this invention to provide a counter for the counting and sizing of particles in an electrolyte dispersion with a high sensitivity, in which the individual particles after their passage through the orifice are available for further analysis and do not mix with other particles of the same dispersion.

According to one embodiment of the present invention a system is provided which comprises a first electrode, an orifice, and a second electrode, and in which a dispersion flows through the orifice, and the first electrode and the second electrode are located at the upstream and downstream sides of the orifice, respectively, and in which a resistance change or impuls is generated by the passage of a dispersion particle through the orifice between the electrodes mentioned above, said resistance impulse being analysed in known manner. According to this invention this counter is characterised in that the orifice is in the dispersion flow path between an entrance channel and an exit channel, and that the electrodes are located in open containers outside the flow path of the dispersion.

Preferably, the entrance channel starts from a first container filled with dispersion in which the first electrode is also located. At the downstream side of the orifice at least one side channel is provided which leads from the exit channel to a second open container filled with pure electrolyte which flow into the exit channel; this second container contains the second electrode. In this manner the electric circuit between the first and second electrodes through the orifice makes the operation of the counter possible. Clearly, it is necessary that the entrance channel and the side channel are short and of large crossection so that the combined electrical resistance of the mentioned channels is smaller or not more than comparable to the resistance defined by the orifice, although when using electrical current sources of very high quality these requirements are not so stringent. Obviously, the counter is more sensitive when the electrical resistances of the channels are negligibly small relative to that of the orifice resistance.

The advantages of the above described invention are that the particles (cells) after passing through the orifice continue the flow movement in the exit channel which is of only somewhat larger crossection than that of the orifice. In this manner the particles remain in that sequence in which they pass through the orifice for being counted and sized, and in this manner they are available for further coincidence needing analyses. The counter according to the invention, heretofore also called Channel-Counter, therefore can be an integral part of other measuring equipment such as a Flow-through-Photometer, known from the German Patent No. P 19 19 628, which is capable of measuring such important cell quantities as nucleic acides and/or proteines. Furthermore, clearly, it is possible to integrate such a counter with a sorter to sort particles (cells) from a mixture as a function of an arbitrarily chosen quantity which can be measured at about the same time as the individual particles pass through the counter orifice.

Another advantage of the channel counter of the present invention is that the two electrodes are located at the exterior of the device in only loosely covered containers of arbitrary size, thus the gas produced during electrolysis can freely leave the system. Thus, the gas does not disturb the operation of the counter by flowing through the orifice where the gas bubbles would be counted as particles since their conductivity is surely different from any electrolyte. Further, because the size of the electrodes can be arbitrarily large in such an electrode configuration the noise level of the counter is low since the generated gas changes the total electrode surface only negligibly provided that the counter current lies in its normal range.

According to a second embodiment of the invention more than one side channel can be constructed which are also at the downstream side of the orifice and the electrolyte from these side channels also flow into the exit channel and these side channels can originate at the same or separate containers as the first side channel; in the latter case it is necessary to divide the second electrode into more than one part in order to achieve symmetry not only in the flow of the electrolyte but also in the electric field, i.e. in the electric current distribution at the orifice.

In order to provide the channel counter of the present invention with a hydrodynamically focused dispersion stream as described by U. Zimmermann et al., in the above mentioned publication, the dispersion should flow through a dispersion channel coaxially aligned in the entrance channel and having a downstream end nozzle at the upstream side of the orifice in such a manner that the particle free electrolyte, which now flows from the first container through the entrance channel, will form an envelope stream around the dispersion stream generally called axis-, or central-stream. In this embodiment of the channel counter the first electrode is located in the first container as in the nonfocused version; no electrode is needed in the additional suspension container (usually of very small size).

The advantage of this embodiment is that the central-stream remains in the middle of the exit channel due to the hydrodynamically focused geometry and due to the inflow of the liquid electrolyte from a plurality, i.e. two opposite sides into the exit channel. Thus, the particles flow through the orifice without distortion of the central-stream which arrangement is better both for the counter and for other sensing devices such as the flow-through-photometer; the symmetrically flowing central-stream can further be very useful where the counter is connected directly to the devices such as a particle (cell) sorter mentioned earlier.

In order to achieve laminar conditions everywhere in the device all of the channels at their junctions, i.e., at the orifice have a conical shape which is for the side channels furthermore bent such that the very end of the side channels is about tangentially arranged with respect to the axis of the exit channel.

The cross section of the exit channel is preferably about $10^4$ to $10^5$ micron$^2$. From the geometry of the device described above it results that the cross section of the orifice is smaller than that of the exit channel. The exit channel can also be split into more than one end channel in case this proves to be necessary for the use of other integrated measuring devices.

The above device i.e., the channels described above should be cut out from electrically isolating material or from an electrically nonisolating material with isolating coating layers; the latter should be chemically inert in order to avoid corrosion or chemical contamination of the occasionally very sensitive dispersion electrolyte.

Preferably, platinum is used for the electrodes with total contact surface of about a few cm$^2$ for each electrodes in order to reduce the noise level of the counter arising from the gas production at the electrodes mentioned above, to a neglectable value. The introduction of such large electrodes is possible because the containers for the electrodes can be of arbitrary size. Furthermore, the electric counter current should be within the range from 0,1 to a few milliamperes bcause for smaller currents the influence of the polarisation potential between the metal electrode and the electrolyte produces undesirable high electrical contact resistance and noise both reducing the sensitivity of the counter.

Another preferred embodiment of the invention is characterised as follows: When the electrodes are very large so that the produced gas can be absorbed by the electrolyte in molecular form, the electrodes are not anymore located in the respective containers but are preferably built into the device at the very vicinity of the orifice in the respective channels at locations at which the channels are still of large cross section. This embodiment has the advantage that the produced gas will not disturb the operation of the counter. Further, such an advantageous location of the electrodes reduces the interelectrode resistance which is desirable when a constant voltage source is used. For constant current sources the above described variation will also result in an improvement on the signal to noise ratio.

In this embodiment of the invention the electrodes are located in the respective channels, i.e. in the entrance channel—around the nozzle for hydrodynamically focusing the suspension, in case this nozzle is provided—and in the side channels—right downstream the orifice. The location and the shape of the electrodes are selected such that they do not disturb the flow of the electrolyte. It is advantageous to use either cylindrical or helical electrodes, having the form of a sheet, a foil or a wire; however, the electrodes can have any arbitrary form.

According to the invention the electrodes may also form an integral part of the inner wall of the corresponding channels.

When the electrodes are, according to the above described embodiment of the invention, located within respective channels of the device the containers need not to be in the very vicinity of the device anylonger. Instead, the electrolyte supply can be provided by arbitrarily long flexible tubes from separate bottles. Separate bottles are needed in this case too in order to prevent short circuiting of the orifice through the same bottle. By such a more flexible version of the invention the device can be handled easier.

According to the invention it is possible to add and use the counter of the invention together with a flow-through-photometer, such as the one identified by German Pat. No. 1,919,628. In such a case the device of this invention should be of such a shape that the optical axis of the flow-through-photometer goes either through the previously described orifice of the counter or in the vicinity of it and is directed at an angle not larger than 45° with respect to the direction of the particle (cell) flow. The channel system here may be covered with microscope coverglass, and the aperture of the ocular is preferably only so large that the microscope sees only a small area of the channel system. In the hydrodynamically focused dispersion stream embodiment the diameter of this area can be smaller than the width of the entrance channel or smaller even than the diameter of the orifice. With such a device the counting and sizing of the cells or the like can be combined with simultaneous measurements of flourometric data such as the nucleic acides and/or proteines and/or the triggering of other electronic devices, e.g. equipment for noise reduction.

Additionally, the described embodiments of the invention can be integrated readily to the sorter described in the U.S. Ser. No. 888,900, filed Mar. 22, 1978. With such a sorter cells can be sorted in accordance with their size, nucleic acid and/or protein content. Simultaneously, the distribution of these quantities can be recorded.

These and other features and objects of the present invention will become more apparent upon a perusal of the following description taken in conjunction with the accompanying drawings wherein:

FIG. 1 is a schematic view of a first counter embodying the present invention;

FIG. 2 is a schematic view of a second embodiment of the counter with hydrodynamical focusing;

Figure 3:
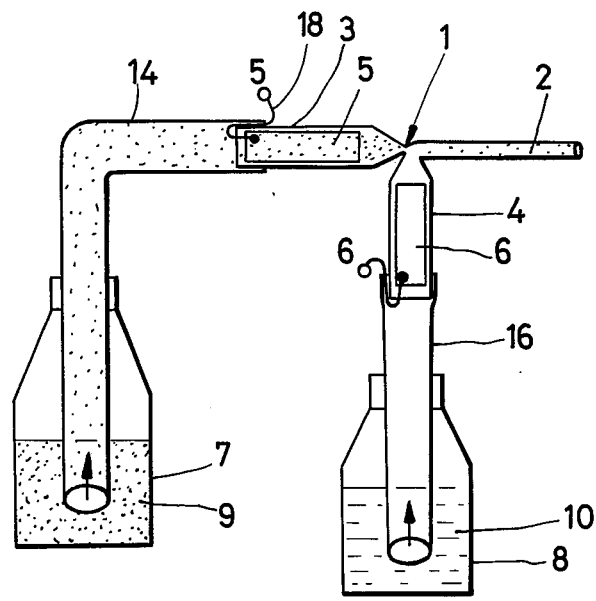
FIG. 3 is a schematic view of a third embodiment of the invention.

FIG. 1 shows the first embodiment of the invented counter. A first container contains the dispersion 9 which consists of the electrolyte and of the particles (cells) suspended in the electrolyte. The dispersion 9 flows through the entrance channel 3, the upstream end of which is immersed in the dispersion 9 whereas its downstream end being conically tapered into the orifice 1. At the downstream side of the orifice 1 the exit channel is arranged through which the dispersion is led to further analytical devices. To the downstream side of the orifice 1 joins also a side channel 4, its conically tapered downstream end leading into the exit channel 2. The other end of the side channel 4 is immersed into pure particle free electrolyte 10 which is stored in the container 8. The first platinum electrode 5 is located in the first container 7 preferably in such a manner that the electrode does not lie directly under the entrance channel 3 in order to avoid the entrance of gas bubbles into channel 3 from electrode 5; similarly, the second platinum electrode 6 is also located in the container 8 in a preselected distance from the entrance of side channel 4. The dispersion 9 flows through the entrance channel 3, the orifice 1, and the exit channel 2 because of the differential pressure applied by a suction pump for example (not shown) between the upstream end of the entrance channel 3 and the downstream end of the exit channel 2. Pure particle free electrolyte flows from the second container 8 into the side channel 4 the downstream end of which is located right after the orifice 1, and then into the exit channel 2. The cross section of the entrance channel, side channel and exit channel is several times larger than that of the orifice 1. The cross section of the orifice, which can be considered as a very short channel is of the order of $100 \times 100$ (micron)$^2$, or smaller. The total surface of both of the electrodes (platinum) is several cm$^2$ each. When a particle of the dispersion 9 passes through the orifice 1 then, supposing different electrical conductivity of the particles and the dispersion, the counter resistance $R_c$ determined between the platinum electrodes 5 and 6 will be somewhat different from the quiescent value of the counter resistance $R_c$.

The current and/or voltage impulse corresponding to the above described resistance impulse will then be transmitted to other equipments where the actual size of the particle can be obtained by electronical standard methods.

FIG. 2 shows another embodiment of the invention comprising two side channels 4', 4" located symmetrically to the exit channel 2 and hydrodynamical focusing means 12 for the dispersion 9. The second electrode is divided into two partelectrodes 6', 6", which are immersed into the containers 8' and 8", respectively, the latters being filled with particle free electrolyte. This embodiment of the invention can be constructed such that the side channels 4' and 4" alternatively end in the same container; this causes some simplification in the construction and operation of the device. The electrolyte 10', 10" flows through the side channels 4', 4" which start from the containers 8' and 8" where the partelectrodes 6' and 6" are located; the side channels 4' and 4" have their tapered downstream ends in close vicinity of the downstream side of the orifice 1, symmetrically to the exit channel 2. The dispersion capillary 12 is located substantially coaxial within the entrance channel 3 and has a nozzle ending in front of the orifice 1. By the focusing effect of the electrolyte flowing in the entrance channel 3 the dispersion 9 contained in container 13" is urged to flow through the center of the orifice 1 in the form of a very thin stream with a diameter of a few microns ($10^{-6}$ m) where the electric field is quasi homogeneous. By this arrangement the optimal accuracy is achieved for the determination of the particle volume by measuring the electrical current and/or the voltage between electrode 5 and the joined electrodes 6' and 6".

Instead of two containers 8' and 8" and partelectrodes 6' and 6" only one container 8 and correspondingly only one electrode 6 may be used. In such a case, when the construction requirements permit this, the invention is somewhat simplified. Thus, this construction simplifies the maintenance of the device.

FIG. 3 shows a third asymmetrical embodiment of the invented counter. The first container 7 contains the dispersion or suspension 9 consisting of the suspended particles and of the electrolyte. The suspension 9 flows in a flexible connection tube 14 immersed in the suspension 9 through the entrance channel 3 with a tapered downstream end which ends at the orifice 1. The relatively thin exit channel 2 is connected at the orifice 1. The dispersion passes through the exit channel and can be transmitted to other measuring equipment afterwards. At the very vicinity of the orifice the tapered end of the side channel 4 enters the exit channel 2. The particle free electrolyte 10 passes from the container 8 through another flexible connection tube into the side channel 4 and into the exit channel 2.

In this embodiment of the invention the platinum electrode 5 is located adjacent the orifice 1 within the entrance channel 3. Correspondingly, another platinum electrode 6' is located inside of the side channel 4 adjacent the orifice 1. It is possible to connect this device to electrical measuring circuit (not shown) by terminals 5", 6". Dispersion 9 and the electrolyte 10 flow under the influence of differential pressure (exerted by suction means, not shown) from the containers 7 and 8 to the end of the exit channel. The cross section of the entrance channel and the side channel are several times larger than that of the orifice 1. The cross section of the exit channel 2 is also somewhat larger than that of the orifice 1; the latter being about $100 \times 100$ (micron)$^2$ or smaller.

Figure 4:
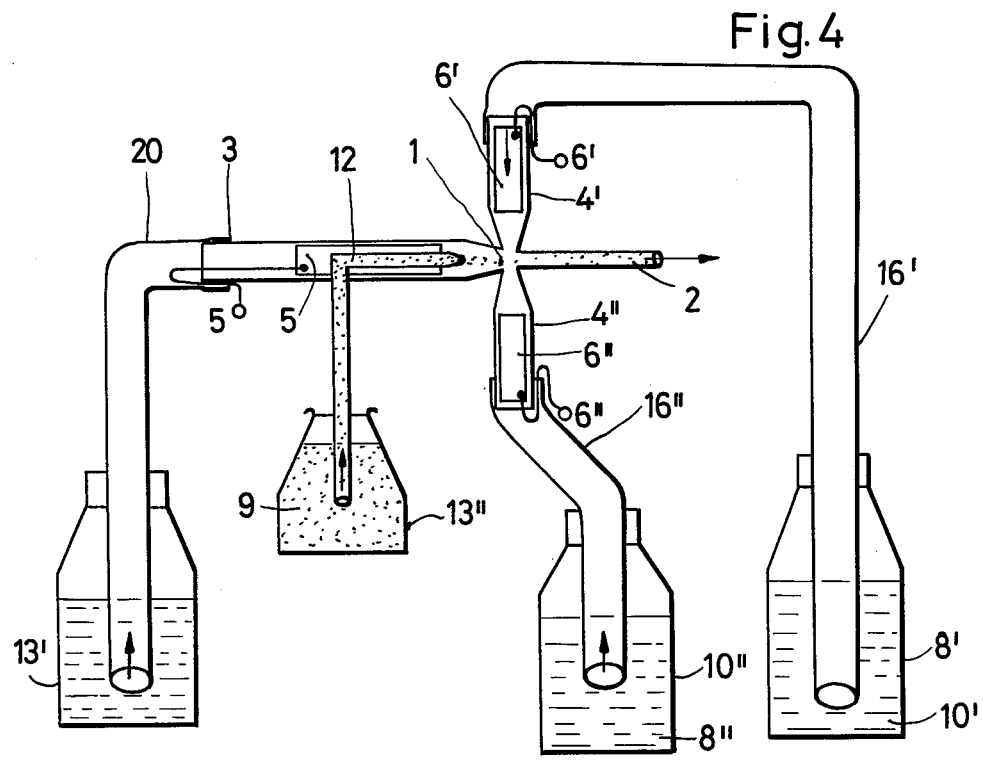
FIG. 4 is a schematic view of a fourth embodiment of the counter according to the invention with hydrodynamical focusing.

FIG. 4 shows a fourth embodiment of the invented device with two symmetrically constructed side connection channels 4' and 4" and hydrodynamical focusing means. In this version the second electrode is divided into partelectrodes 6' and 6" which are located in the side channels 4' and 4", resp, adjacent the orifice 1. The channels 4' and 4" are connected via flexible tubes 16' and 16" to the electrolyte containers 8' and 8". The side channels 4' and 4" are located adjacent the downstream side of the orifice 1 such that the electrolyte from the side channels flows symmetrically into the exit channel 2. The dispersion channel 12 may enter into the entrance channel 3 through its side wall in coaxial alignment with the entrance channel 3 similarly to the arrangement of FIG. 2 and produces a very thin dispersion stream flowing through the center of the orifice with the same result as described above. The first electrode 5 is located completely inside the entrance channel 3 which is connected to the particle free electrolyte container 13' via a flexible tube. The dispersion 9 on the other hand, is contained in the container 13". The advantages of the hydrodynamical focusing and of the symmetrical or quasi concentrical flow of the dispersion through the orifice 1 and the exit channel were already given in connection with FIG. 2.

In FIGS. 3 and 4 the containers 7, 8, 8', 8", 13', 13", are shown as bottles which are the more usual receptacles in laboratories and are available in a large number of various forms.

Figure 5:
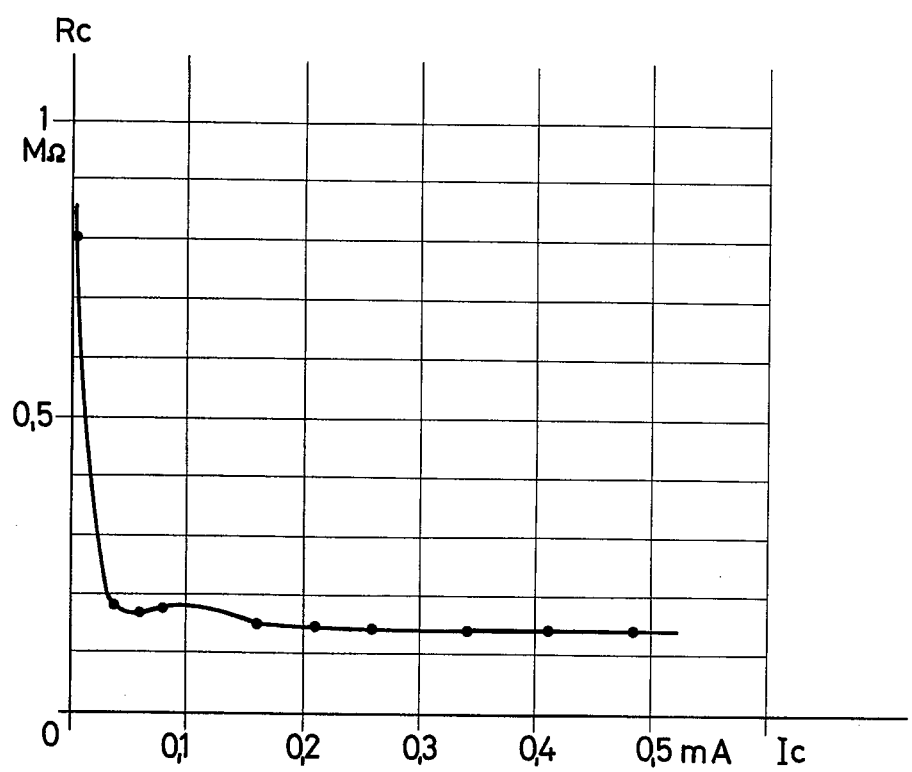
FIG. 5 is a graph of the interelectrode resistance of a model of the invention as function of the counter current.

FIG. 5 shows the quiescent counter resistance $R_c$, measured between the platinum electrodes as a function of the quiescent counter current, the total surface of each electrode lying between 2 and 3 cm². In this figure the strong influence of the polarisation potential difference is clearly shown which develops between any metal and an electrolyte having specific conductivity much lower than that of the metal. At such very low electric currents a large part of the counter resistance substantially consists of this resistance. Therefore, when voltage sources are used to apply a potential difference between the electrodes of the counter the sensitivity of the counter is low for such low currents. When using current sources to energize the counter, the electrical noise level is large for such low current values, since the above mentioned polarisation potential substantially exists at the junction between the metal (platinum in this case) and the electrolyte and the space charge of this junction is always subject to fluctuations causing noise in the circuit. From FIG. 5 follows that good operation of counters with electrode surfaces in the range of one cm² will be achieved for currents above 0,1 milliamperes.

In view of the foregoing description it will be appreciated that many modifications and variations of the subject invention will be apparent to those skilled in the art. It is to be understood, therefore, that the scope of this invention is limited only in accordance with the following claims.

I claim:

1. An apparatus for counting and sizing particles suspended in a liquid electrolyte, comprising, in combination:
   (1) a first vessel for first liquid electrolyte having particles to be counted and sized suspended therein;
   (2) a second vessel for particle-free second liquid electrolyte;
   (3) a first electrode immersed in the first liquid electrolyte;
   (4) a second electrode immersed in the second liquid electrolyte;
   (5) an orifice having upstream and downstream sides and constituting a first particle-observing location in fluid flow connection on its upstream side with the first vessel and sized to allow one particle at a time to pass therethrough; the passage of a particle through the orifice being sensed as a change in electrical resistance at the orifice and measured at the electrodes;
   (6) a first fluid flow passage connecting the first vessel with the upstream side of the orifice for flow of first liquid electrolyte from the vessel to the orifice;
   (7) a second fluid flow passage in fluid flow connection with the second vessel and with the downstream side of the orifice or flow of second liquid electrolyte from the vessel to the downstream side of the orifice;
   (8) a third fluid flow passage directly interconnecting the downstream side of the orifice and the second fluid flow passage with a second-particle-observing location for carrying first and second liquid electrolyte and particles away from the orifice to the second particle-observing location; and sized throughout its length to carry the particles in the same sequence of flow as that in which they pass through the orifice to facilitate observation in that order at the second particle-observing location; and
   (9) means for drawing first and second liquid electrolyte and particles in the third fluid flow passage from each of the first vessel through the orifice and the second vessel to the second particle-observing location.

2. An apparatus according to claim 1 in which the first electrode is immersed in the first liquid electrolyte in the first vessel, and the second electrode is immersed in the second liquid electrolyte in the second vessel.

3. An apparatus according to claim 1 in which the first electrode is immersed in the first liquid electrolyte in the first fluid flow passage; and the second electrode is immersed in the second liquid electrolyte in the second fluid flow passage.

4. An apparatus according to claim 1 having two second electrodes and two second vessels for particle-free second liquid electrolyte, each in fluid flow connection with the downstream side of the orifice, one first electrode and two first vessels for first liquid electrolyte; one first vessel containing the electrode, and the other first vessel containing particle-containing first liquid electrolyte; and a hydrodynamical focusing capillary in flow connection with the other first vessel and directing a thin stream of particle-containing electrolyte into the center of the orifice.

5. An apparatus according to claim 4 in which each of the first vessels is in separate fluid flow connection via separate fluid flow passages to the upstream side of the orifice; one first electrode and two first vessels for first liquid electrolyte; one first vessel containing the electrode, and the other first vessel containing particle-containing first liquid electrolyte; and a hydrodynamical focusing capillary in flow connection with the other first vessel and directing a thin stream of particle-containing electrolyte into the center of the orifice.

6. An apparatus according to claim 4 in which each of the second vessels is in separate fluid flow connection via separate fluid flow passages to the downstream side of the orifice.

7. An apparatus according to claim 6 in which the first electrode is immersed in the first liquid electrolyte in the first flow passage; and each of the second electrodes is immersed in second liquid electrolyte, one in each of the separate fluid flow passages.

8. An apparatus according to claim 1 in which each of the first and second electrodes is immersed in a body of first and second liquid electrolyte, respectively, the surfaces of which bodies of electrolyte are open to the atmosphere, for escape into the atmosphere of gases generated at the electrodes for flow of particle-free second liquid electrolyte to the downstream side of the orifice and the third fluid flow passage, one first electrode and two first vessels for first liquid electrolyte; one first vessel containing particle free first liquid electrolyte, and the other first vessel containing particle-containing first liquid electrolyte; and a hydrodynamical focusing capillary in flow connection with the other first vessel and directing a thin stream of particle-containing electrolyte into the center of the orifice.

21. An apparatus according to claim 19 in which the first fluid flow passage defines a capillary nozzle at the